(12) United States Patent
McEnany et al.

(10) Patent No.: US 6,512,955 B1
(45) Date of Patent: Jan. 28, 2003

(54) ELECTRICAL APPARATUS FOR THERAPEUTIC TREATMENT

(76) Inventors: Thomas J. McEnany, 2006 Salt Myrtle La., Orange Park, FL (US) 32073; Michael Carroll, 2415 Dumfries Ct., Orange Park, FL (US) 32065

(*) Notice: Subject to any disclaimer, the term of this patent is extended or adjusted under 35 U.S.C. 154(b) by 237 days.

(21) Appl. No.: 09/633,673

(22) Filed: Aug. 7, 2000

(51) Int. Cl.⁷ ................................................ A61N 1/32
(52) U.S. Cl. .............................. 607/72; 607/46; 607/48; 607/63; 607/70; 607/49; 607/67
(58) Field of Search .................. 607/46, 48–49, 607/50, 59, 63, 67, 66, 70, 72–76

(56) References Cited

U.S. PATENT DOCUMENTS

| | | | |
|---|---|---|---|
| 3,908,669 A | * 9/1975 | Man et al. ................ | 128/422 |
| 4,453,548 A | * 6/1984 | Maurer et al. ............. | 128/421 |
| 4,541,432 A | * 9/1985 | Molina-Negro et al. ... | 128/421 |
| RE32,091 E | * 3/1986 | Stanton .................... | 128/423 |
| 5,010,896 A | * 4/1991 | Westbrook ................ | 128/798 |
| 5,041,974 A | 8/1991 | Walker et al. | |
| 5,052,391 A | 10/1991 | Silberstone et al. | |
| 5,063,929 A | 11/1991 | Bartelt et al. | |
| 5,065,083 A | 11/1991 | Owens | |
| 5,067,495 A | * 11/1991 | Brehm ..................... | 128/421 |
| 5,158,081 A | * 10/1992 | McWhorter et al. ...... | 128/421 |
| 5,169,384 A | 12/1992 | Bosniak et al. | |
| 5,217,009 A | 6/1993 | Kronberg | |
| 5,269,303 A | 12/1993 | Wernicke et al. | |
| 5,273,033 A | 12/1993 | Hoffman | |
| 5,562,718 A | * 10/1996 | Palermo .................... | 607/46 |
| 5,626,619 A | 5/1997 | Jacobson et al. | |

FOREIGN PATENT DOCUMENTS

| | | |
|---|---|---|
| EP | 0009920 | 4/1980 |
| EP | 0010364 | 4/1980 |
| EP | 0052087 | 5/1982 |
| EP | 0057048 | 8/1982 |
| EP | 0087617 | 9/1983 |
| EP | 0196393 | 10/1986 |
| EP | 0197889 | 10/1986 |
| EP | 0203336 | 12/1986 |
| EP | 0248913 | 12/1987 |
| EP | 0290126 | 11/1988 |
| EP | 0354578 | 2/1990 |
| EP | 0359982 | 3/1990 |
| EP | 0391428 | 10/1990 |
| EP | 0425673 | 5/1991 |
| EP | 0445359 | 9/1991 |
| EP | 0459945 | 12/1991 |
| EP | 0486177 | 5/1992 |

(List continued on next page.)

Primary Examiner—Joseph Pelham
Assistant Examiner—Shawntina T. Fuqua (57) ABSTRACT

A system and method for generating high voltage, pulsed electrical stimulation to a patient for therapeutic treatment. The apparatus includes a voltage controlled pulse generator network that provides an output waveform including three monophasic pulses. This waveform is output to an electrode set including two active electrodes and one ground electrode. The triple pulse monophasic wave pattern is capable of reverse polarities. Each electrode in the electrode set generates independently variable intensities, while still using the common ground element. The voltage output of each active electrode is independently variable with respect to each other. The pulse generator network may be controlled using a processor, and in particular, a microprocessor, for example. A common control pulse is initially generated. The control pulse triggers dual trigger pulses. Each trigger pulse includes three monophasic pulses. These pulses may be spaced 100 microseconds apart in accordance with one embodiment of the invention. This waveform is fed into two independently controllable voltage controlled output circuits. Each of the voltage controlled output circuits in turn output to the common ground electrode and respective active electrodes.

14 Claims, 5 Drawing Sheets

FOREIGN PATENT DOCUMENTS

| | | |
|---|---|---|
| EP | 0561068 | 9/1993 |
| EP | 0573946 | 12/1993 |
| EP | 0611583 | 8/1994 |
| EP | 0620025 | 10/1994 |
| EP | 0623362 | 11/1994 |
| EP | 0645162 | 3/1995 |
| WO | 8201656 | 5/1982 |
| WO | 8707511 | 12/1987 |
| WO | 9004997 | 5/1990 |
| WO | 9011798 | 10/1990 |
| WO | 9014127 | 11/1990 |
| WO | 9213592 | 8/1992 |
| WO | 9219318 | 11/1992 |
| WO | 9301862 | 2/1993 |
| WO | 9302740 | 2/1993 |

* cited by examiner

ELECTRICAL APPARATUS FOR THERAPEUTIC TREATMENT

BACKGROUND OF THE INVENTION

1. Field of the Invention

The invention relates broadly to a system and method for stimulation of a portion of a living body by applying pulsed electrical impulses. In particular, the system and method of the invention relates to neuromuscular stimulation of a patient by applying pulsed electrical impulses.

2. Description of the Related Art

Conventional apparatuses for transcutaneous, i.e., through the skin, electrical stimulation of nerves and muscles using pulse generators are well known in the art. These apparatuses provide neuromuscular stimulation by outputting pulsed electrical impulses having characteristics of varying amplitudes and frequencies. Illustratively, a typical apparatus includes a voltage control circuit or network. This voltage control circuit or network produces pulsed electrical impulses. A single ground electrode with two active electrodes in dual output, or alternatively, independent sets of active electrodes and grounds, delivers the electrical stimulation to the patient.

These electrical impulses are commonly monophasic in nature in conventional apparatuses. That is, the impulses do not alternate between positive and negative polarity. Rather, the pulses remain positive throughout the duration of the pulse or, alternatively, remain negative throughout the duration of the pulse. The monophasic pulses conventionally include a twin peak configuration having a fixed duration. The electrodes may be in the form of pads, which are positioned on the skin of the patient, for example. However, there are various deficiencies associated with the conventional apparatuses.

SUMMARY OF THE INVENTION

In the conventional apparatuses and techniques, it is desirable to be able to control the voltage delivered through the dual electrodes. In particular, it is desirable to be able to variably adjust the voltage delivered through the each active electrode independently. However, the conventional apparatuses are limited in this respect.

In conventional apparatuses, the dual outputs in each active electrode are not independent of each other. As a result, both active electrodes share any change in output experienced by one of the active electrodes. Accordingly, individual adjustments between the two active electrodes cannot be performed. Some conventional apparatuses have attempted to overcome this dependence between electrodes.

That is, in conventional devices, it is known to utilize two separate voltage controlled pulse generator networks to achieve independent outputs through such electrodes. In such conventional apparatuses, these two separate voltage controlled pulse generator networks each includes an active electrode and a ground electrode corresponding to each voltage controlled network. However, it should be appreciated that in actuality this is merely the combination of two basic electrical stimulators within one unit. The system and method of the invention address these and other deficiencies of the conventional apparatuses.

Accordingly, it is an object of the system and method of the invention to provide an electrical stimulator apparatus for therapeutic treatment of a patient that generates a unique triple pulse monophasic waveform in either a monophasic or bi-phasic setting.

It is a further object of the system and method of the invention to provide an electrical stimulator apparatus for therapeutic treatment of a patient having dual independently controllable, active output electrodes.

It is a further object of the invention to provide an electrical stimulator apparatus possessing the capability of reversible polarity and independent control of the voltage output to the active electrodes.

In accordance with the system and method of the invention, an apparatus is provided for generating a high voltage, pulsed electrical stimulation transcutaneously to a patient for therapeutic neuromuscular treatment. In accordance with the invention, the apparatus includes a voltage controlled pulse generator network that provides an output waveform including three monophasic pulses. This waveform is output to an electrode set including two active electrodes and one ground electrode. The triple pulse monophasic wave pattern is capable of reverse polarities.

Further, in accordance with the invention, each electrode in the electrode set generates independently variable intensities, while still using the common ground element. The voltage output of each active electrode is independently variable with respect to each other. The pulse generator network may be controlled using a processor, and in particular, a microprocessor, for example. A common control pulse is initially generated. The control pulse triggers a trigger pulse. The trigger pulse includes the three monophasic pulses. These variably spaced pulses are normally 100 microseconds apart in accordance with one embodiment of the invention. This waveform is fed into two independently controllable voltage controlled output circuits. Each of the voltage controlled output circuits in turn output to respective active electrodes. Accordingly, the system and method of the invention adds an additional voltage controlled pulse to the traditional twin peak monophasic output. As a result, more energy content is transferred to the affected area of the patient, while providing a measurable increase in patient comfort. Additionally, independent testing in development of the system and method of the invention has shown a twenty-percent improvement in patient outcomes over conventional pulse pairs.

BRIEF DESCRIPTION OF THE DRAWINGS

These and other aspects of the invention will become apparent from the following description, which illustrate exemplary embodiments of the invention when read in conjunction with the accompanying drawings, in which.

DETAILED DESCRIPTION OF THE PREFERRED EMBODIMENTS

In accordance with the system and method of the invention, an apparatus is provided for generating a high voltage, pulsed electrical stimulation transcutaneously to a patient for therapeutic neuromuscular treatment. In accordance with the invention, the apparatus includes a voltage controlled pulse generator network that provides an output waveform including three monophasic pulses. This waveform is output to an electrode set including two active electrodes and one ground electrode. The triple pulse monophasic wave pattern is capable of reverse polarities.

Further, in accordance with the invention, each active electrode in the electrode set generates independently variable intensities, while still using the common ground element. The voltage output of each active electrode is independently variable with respect to each other.

In further explanation of the system and method of the invention, the control pulse is frequency controlled and normally generated in one form from 1 pulse per second (PPS) to 100 PPS. These generated pulses are used to trigger the timing circuit. When triggered, the timing circuit generates the pulsed output, which is a trio of pulses. This pulsed output may be characterized as trigger pulse A and trigger pulse B if used in a dual channel environment. Each of the trigger pulse A and the trigger pulse B correspond to a respective channel. The trigger pulse A and trigger pulse B trigger the discharge of respective voltage controlled capacitors placing a direct current discharge across the active and ground electrodes, which are positioned on the patient. Further, the intensity level of the discharged direct current for each channel may be independently controlled.

In accordance with the system and method of the invention, a suitable mode selection apparatus or switch provides selection of two different modes of operation. These modes may be characterized as a "continuous mode" and an "alternating mode." The two respective active electrodes may be characterized as operating on the respective channels. Corresponding trigger pulses A and B, as described above triggers the pulses in each channel. Accordingly, one active electrode operates on "channel A." The other active electrode operates on "channel B."

In accordance with the system and method of the invention, in continuous mode, the patient receives pulsed stimulation from the active electrodes simultaneously. In alternating mode, the channel A electrode is operated independently from the channel B electrode. Illustratively, the processor will alternate output between the channel A electrode and the channel B electrode.

It should be appreciated that the method of the invention may be implemented on any of a variety of systems or apparatuses capable of producing and delivering the electrical pulses in accordance with the invention. The present invention provides therapeutic electronic pulses in groups of three. Basically, the device provides a high voltage generator with a controlled DC discharge for topical application to affected areas.

Figure 1:
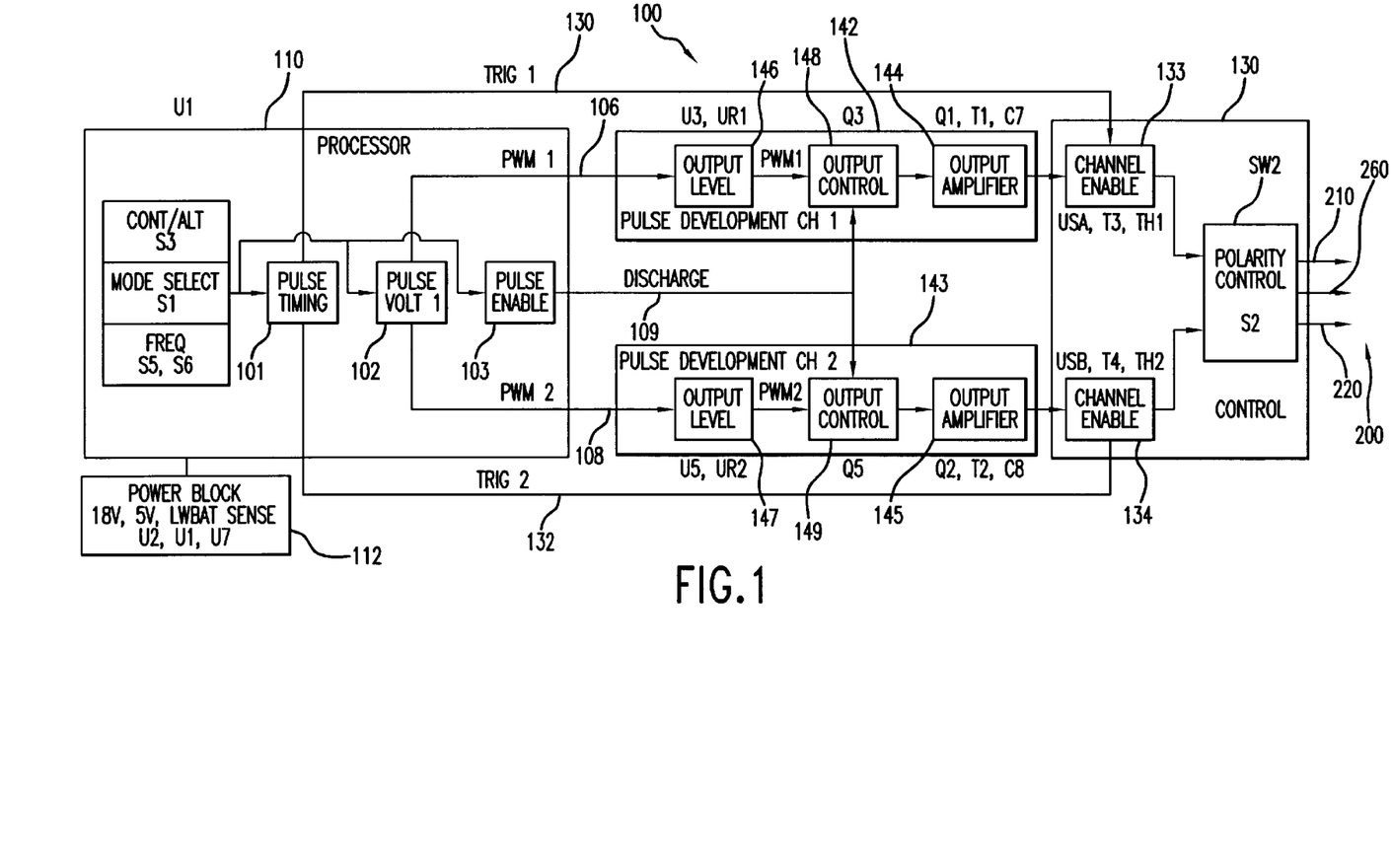
FIG. 1 is a block diagram showing a voltage neuromuscular stimulator in accordance with an embodiment of the system and method of the invention.

With reference to FIG. 1, a high voltage neuro-muscular stimulator that provides three pulses through two channels is illustrated generally at 100, and includes a control portion of 110, dual pulse development portions 142, 143, a discharge portion 130 and an output portion 200. A power supply 112, common to virtually all electronic equipment provides the basic voltage in current for system operation.

The control portion 110 provides two trigger signals 130, 132 and two pulse width modulation (PWM) signals 106, 108. A discharge signal 109 is also provided. The trigger signals 130, 132 are applied to the discharge portion 130, while the PWM signals 106, 108 are applied to the pulse development portions 142, 143, respectively, as is the discharge signal 109. The pulse development portions 142, 143 receive the PWM signals 106, 108 and use the signals to develop the desired output. Once the output pulses are developed, they are sent through output amplifiers 144, 145 to the discharge portion 130 and combined with the trigger signals, 130, 132 in the channel enable sections 133, 134 of the discharge portion 130. These signals go through a polarity control switch SW2 before being discharged to the affected area through an output section 200 including output probes 210, 220 and 260.

The control portion 110 develops the trigger signals in a pulse timing section 101. The PWM signals 106, 108 are developed in a pulse voltage section 102 while the discharge signal 109 is developed in a pulse enable section 103. As will be seen in greater detail hereinafter, the control portion 110 may utilize a single integrated circuit.

Figure 2:
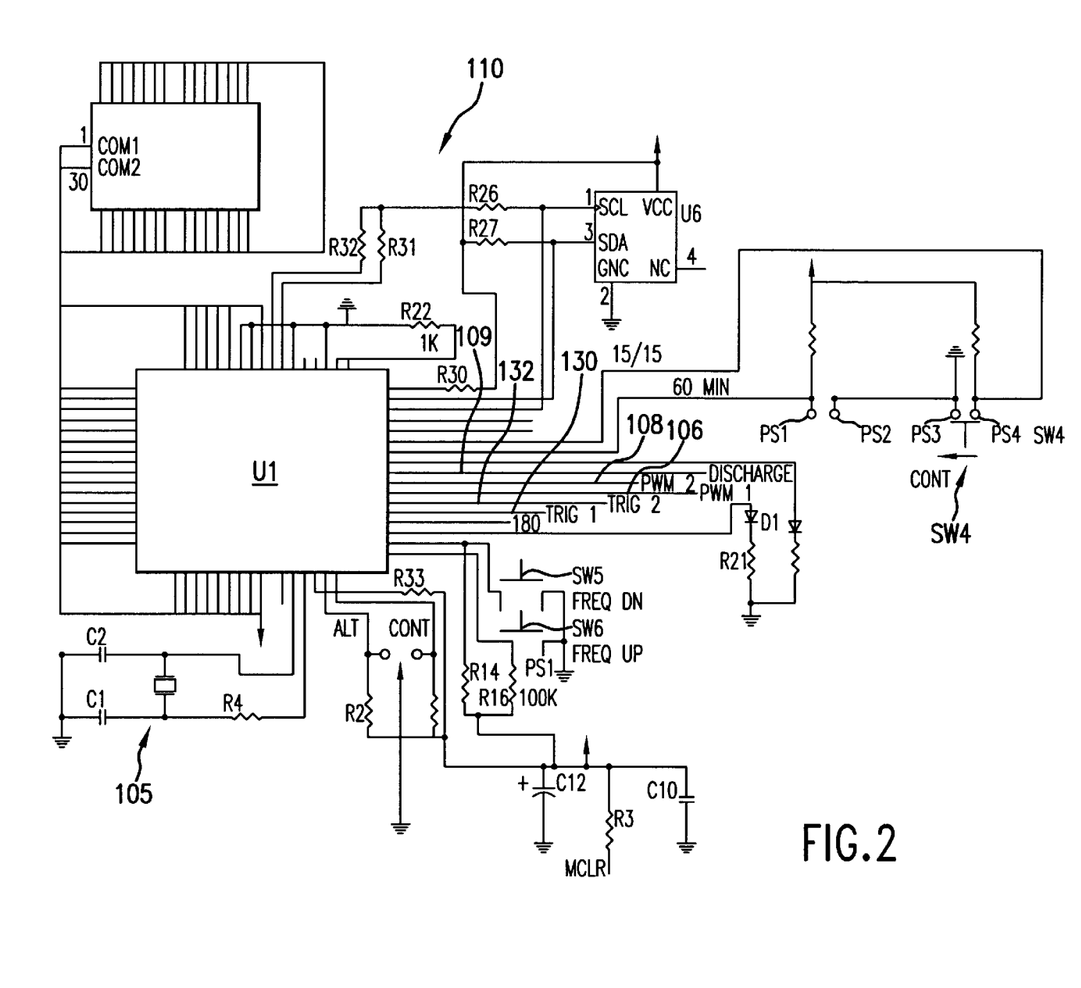
FIG. 2 is a block diagram showing further aspects of the circuitry in accordance with an embodiment of the system and method of the invention.

Turning now to FIG. 2, integrated circuit U1 is the primary control circuitry for the control portion 110. Basic clock frequencies are provided through a crystal oscillator 105. Several switches are associated with the control portion 110. These include a mode control switch SW4, and frequency control switches SW5, SW6 which lower and raise the frequency respectively. The trigger signals 130, 130 and the PWM signals 106, 108 are developed in the integrated circuit U1 110. As can be seen and will be appreciated by those skilled in the art, pull-up resistors are provided in the control portion 110 as seen in FIG. 2. These resistors are necessary to maintain a minimum voltage on unused lines associated with the integrated circuit U1 and therefore ensure controlled operation of the integrated circuit U1.

Figure 3:
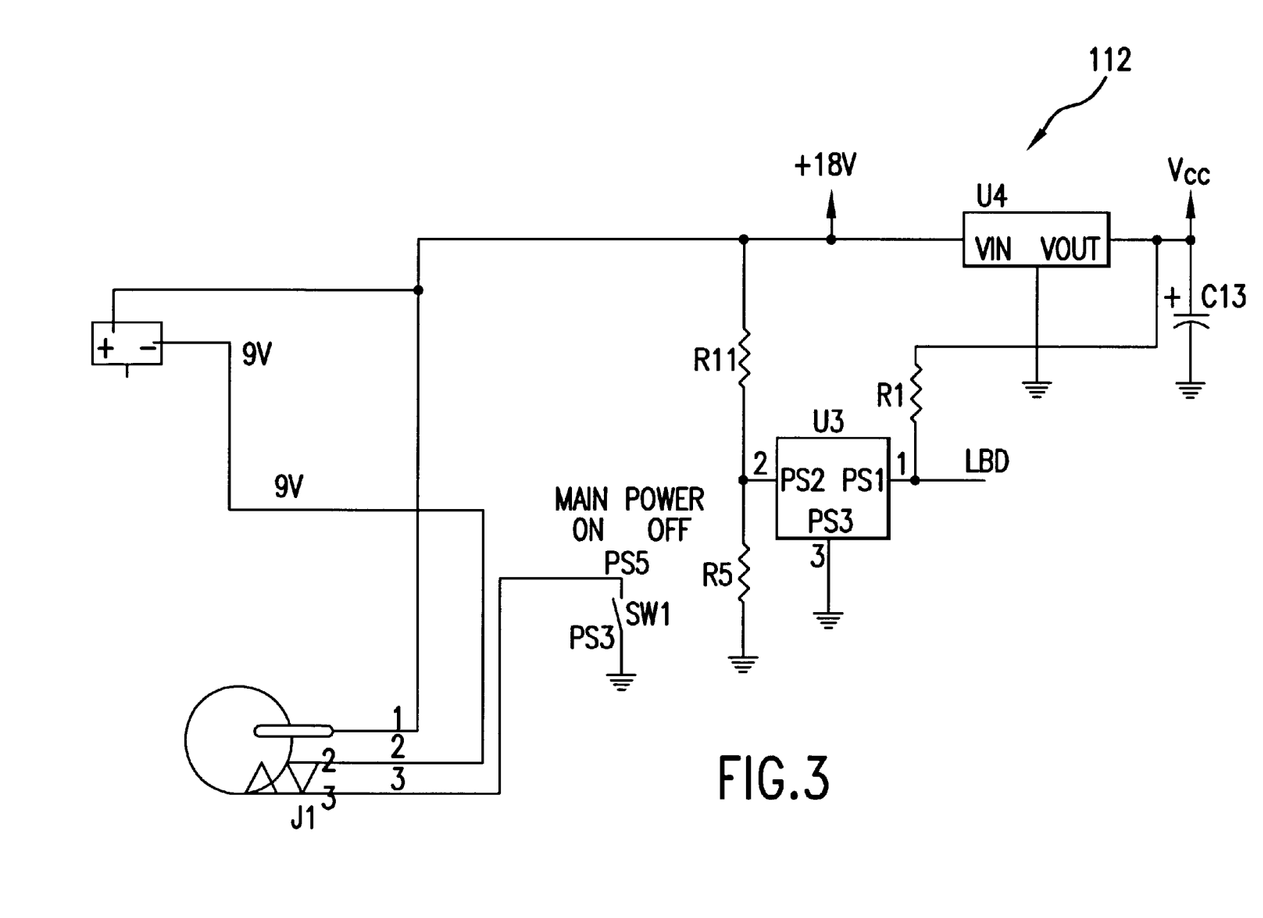
FIG. 3 is a block diagram showing a power supply in accordance with an embodiment of the system and method of the invention.
Figure 4:
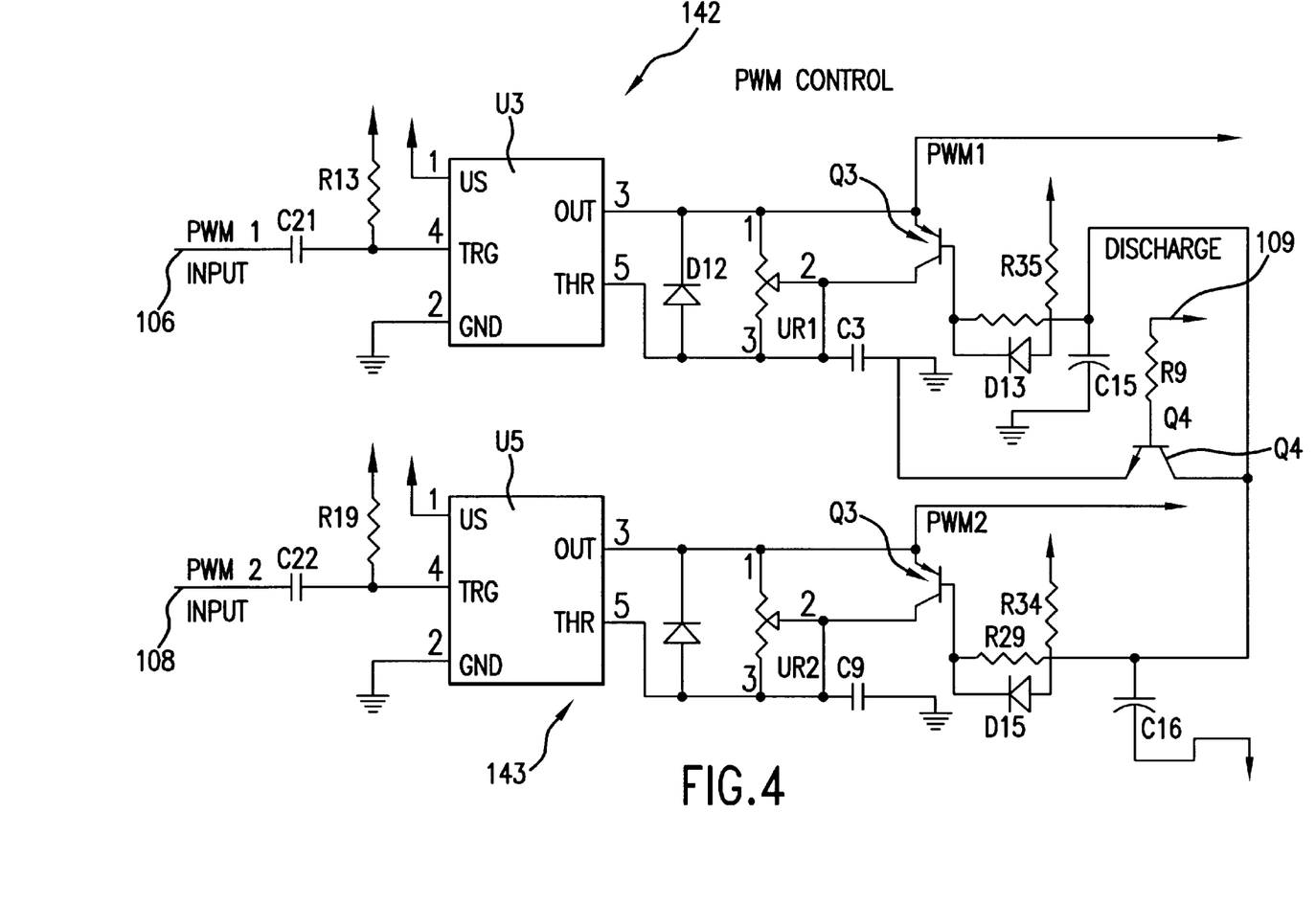
FIG. 4 is a block diagram showing aspects of the pulse development portions in accordance with an embodiment of the system and method of the invention.

Turning now to FIG. 3, the power supply is illustrated generally at 112 and includes components that will be apparent to those skilled in the art. FIG. 4 illustrates the pulse development portions 142, 143. The pulse development portions 142, 143 include two similar circuits that are joined by transistor Q4 which receives the discharge signal on its base to allow the PWM signals to be discharged to the directed portion 130. As seen in FIG. 4, the PWM signals 106, 108 are directed to one shot multivibrators U3, U5 which produce a square wave used to control current to pulse transformers as will be seen in greater detail hereinafter. The multivibrators U3, U5 produce square waves that are applied to the emitters of transistors Q3 and Q5. These transistors Q3 and Q5 act as switches that are controlled by base current received from the discharge signal 109 through transistor Q1. The PWM signals 106, 108 are directed to the output from the output control to the output amplifiers 144, 145 as seen in FIG. 1 in the discharge portion 130.

Figure 5:
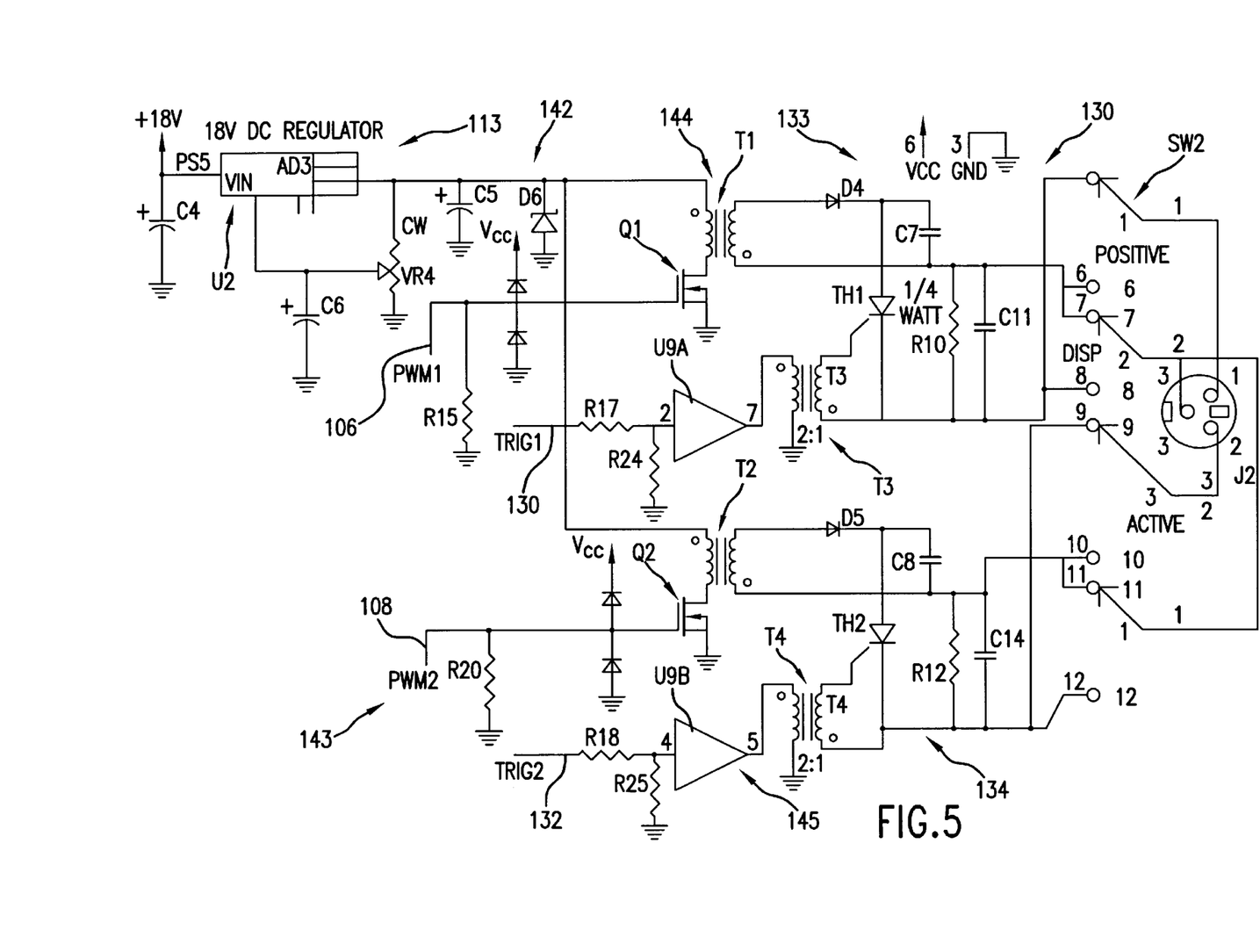
FIG. 5 is a block diagram showing a voltage generator in accordance with an embodiment of the system and method of the invention.

As illustrated in FIG. 5, the PWM signals 106, 108 are applied to the base of field effect transistors Q1, Q2. These field effect transistors, Q1, Q2, as well as the components in a high voltage generation section 133 and other sections of the device utilize voltage and current supplied by an 18 volt DC regulator 42 used to supply voltage and current to the pulse transformers T1 and T2. The pulse transformers T1 and T2 are used to create the output pulses.

Operation of the voltage generation section 133 is based on the PWM signals 106, 108. These signals were developed to control the length of time current is supplied to the primary of the pulse transformers T1, T2. This current directly controls the strength of the magnetic field applied to the secondary of pulse transformers T1, T2. When the PWM signals 106, 108 are terminated, the magnetic field developed will collapse and the secondary will produce a voltage proportional to the strength of the magnetic field which is to be stored by output capacitors C7, C8. The transformer voltage is determined by the pulse width of the square wave applied to the transformers. As can be seen in FIG. 5, these PWM signals 106, 108 are applied to the bases of transistors Q1 and Q2. The voltage is developed across the transformers T1, T2 are stored in capacitor C7, C8 and readied for discharge.

Trigger signals 130, 132 are applied to the base of op-amps U9a and U9b. These low level signals are isolated from the high voltage circuitry associated with the output transformers T1 and T2 through isolation transformers T3 and T4. Through these isolation transformers T3 and T4, the trigger pulses 130, 132 are applied to thiristers TH1, TH2. It should be appreciated that throughout the discussion, a two channel device has been observed and, consequently, the signal generation, pulse development and discharge are occurring simultaneously. Thyristers TH1, TH2 control the discharge of C7 and C8 through switch SW2, which is a polarity reversing switch. The three pulses are applied to each capacitor C7, C8, when selected, at 100 microsecond intervals. Once triggered, the capacitors C7, C8 discharge through SW2, which applies the pulses through output electrodes 210, 220, 260, illustrated in FIG. 1.

While the primary components of the present invention have been described with regard to their circuit arrangement, it will be appreciated by those skilled in the art that certain resistors and capacitors may be used to form filter circuits as necessary and other resistors and capacitors may be used to form biasing circuits for the various transistors and other amplification or switch devices as necessary. Further, blocking diodes and other use of diodes throughout the circuitry will be apparent to those skilled in the art.

As shown in FIG. 1, the stimulator system 100 in accordance with the system and method of the invention provides a voltage controlled neuromuscular stimulation apparatus with two independent outputs including the channel A electrode 210 and channel B electrode 220, which interact with the ground electrode 260.

The operation of the stimulator system 100 in accordance with the system and method of the invention will hereinafter be described with reference to FIGS. 1, 2, 4 and 5. A user will control the frequency of the pulses and the amplitude of the pulses by using the control portion 110 and the switching system provided. These include the mode select switch SW4 for pulses continuous or alternating switch S3 the mode select switch S4, and the frequency control switches S5, S6. The timing of the pulses will be adjustable from one pulse per second to 100 pulses per second. Further, in the continuous mode, the user may receive stimulation from one electrode only for example, electrode 210, associated with channel A. In the alternating mode, the user may receive stimulus from both channels in an alternating mode. Effectively, each channel is capable of producing the three pulses at predetermined time intervals at a predetermined frequency.

Once the user controlled settings are fixed, the various signals can then be developed. The pulse timing circuit 101, as seen in FIG. 1, and as seen in FIG. 2, more specifically as main processor U1, develops trigger signals 130, 132 which are transmitted to op-amps U9a and U9b of the discharge portion 130. The main processor U1 also develops PWM signals 106, 108 which are applied to multivibrators U3, U5 in the pulse development portions 142, 143 and as seen in FIGS. 1 and 4. The discharge signal 109, developed in the pulse enablement section 103 of the main processor U1, as seen in FIG. 2, is applied to the base of transistor Q4, as seen in FIG. 4, which is used to apply a control voltage to the respective bases of output control transistors Q3 and Q5, which also have the square wave PWM signals applied to their emitters, turning them off and releasing the PWM signals 106, 108 for application to the base of transistors Q1 and Q2 in the high voltage section as seen in FIG. 5. The PWM signals 106, 108 are applied through transistors Q1 and Q2 to output transformers T1 and T2 which apply a voltage proportional to the pulse-width of the square wave of the PWM signals 106, 108 to discharge capacitor C7, C8.

Meanwhile, the trigger signals are applied through op-amps U9a and U9b through isolation transformers T3, T4 to thyristors TH1, TH2. These thyristors, TH1, TH2, once receiving the signal allow the output capacitor C7, C8 to discharge through switch SW2 and finally through the electrodes 210, 220 and 260 to provide the three pulses to stimulate a user. The channel enablement section 134 includes op-amps U9a and U9b, isolation transformers T3 and T4, and thyristors TH1 and TH2. The user may select either positive or negative polarity pulses on the active electrodes in the output portion 200 by use of the polarity switch SW2.

In continuous mode, the patient receives pulsed stimulation from both the channel A electrode 210 and the channel B electrode 220 simultaneously. These pulses may be controlled as discussed above. In continuous mode, the pulses will ramp up in intensity for two seconds from 0 volts to a maximum intensity. The maximum intensity may be set by each individual channel intensity level control as controlled by the intensity control portion 142. After ramping up to the maximum intensity, the pulses will then continue pulsing at the set intensity level and pulse repetition rate.

In alternating mode, the channel A electrode 210 is operated independently from the channel B electrode 220. Illustratively, the voltage controlled channel control 130 will control the voltage pump portion 144 to alternate output between the channel A electrode 210, as driven by the first voltage pump 146, and the channel B electrode 220, as driven by the second voltage pump 148. The output for each of the channel A electrode 210 and the channel B electrode 220 may be based on a seven second cycle, in accordance with one embodiment of the invention. That is, in alternating mode, the channel "A" active electrode 210 is initially active, for example. The pulse pairs will ramp up in intensity at a rate set by the master frequency for two seconds. The pulse pairs ramp up to a maximum intensity. Channel "A" will then continue pulsing at the set intensity level and master frequency for five seconds.

In accordance with operation in the alternating mode, after channel A has reached the end of the seven-second cycle, the pulse pairs are applied to the channel B active electrode 220. This output also ramps from 0 volts to the intensity set by the channel B intensity control in the intensity control portion 142. The output ramps up in 2 seconds, for example. The output then continues pulsing for 5 seconds at the set rate and intensity. The cycle starts again with channel "A." Thereafter, the cycle continues in a similar fashion by alternating output between channels "A" and "B" for the 7-second cycle.

As described above, the output portion 200 includes the channel A electrode 210, the channel B electrode 220 and the ground electrode 260. The output portion 200 may be constructed in any suitable manner. However, the particular construction must provide sufficient surface area to safely dissipate the energy contained in the pulses. The electrodes 210, 220 and 260, both active and ground, are usually pads having a relatively large surface area. These pads may be positioned directly on the skin of the patient. The ground electrode pad is usually several times larger than the active electrode pads. Further, it should be appreciated that dual active electrodes utilized in conjunction with the invention are preferable over a single active electrode for increased efficiency in terms of positioning on the patient and delivering of the electrical stimulation.

It should be appreciated that the system and method of the invention are not limited to using pads to transmit the stimulus to the patient. Alternatively, each of the active electrodes and the ground electrode may be in the form of probes, for example.

The figures herein provided illustrate a particular implementation of the stimulator system 100. However, it should be appreciated that the invention is not limited to the arrangement as shown in the Figures. For example, the voltage and pulse might be controlled by the same component, in contrast to the arrangement shown in FIG. 1. Additionally, it should be appreciated that the control portion 110 might utilize some predetermined interrelationship between the mode, voltage and pulse to generate the output of the stimulator system 100, for example. Illustratively, the stimulator system 100 may utilize the alternating mode for a certain range of voltages. Alternatively, the stimulator system 100 might utilize the continuous mode for another range of voltages.

It should be recognized that the control portion 10 does not necessarily have to receive adjustment inputs from a user. Rather, a separate operating system (not shown) may automatically adjust the mode, voltage and pulse rate in the control portion 110. These operating parameters including mode, voltage and pulse rate, as well as polarity, may be automatically adjusted based on the condition of the patient, the number of therapeutic sessions undergone by the patient, or the specific portion of the patient's body to which the stimulus is applied, for example.

It should be appreciated that any of a wide variety of components may be used to construct the stimulator system 100. These components may be in the form of hardware and/or software. illustratively, the control portion 110 could be constructed using variable potentiometers to set voltage and pulse rate levels along with slide switches to select the mode and polarity.

Additionally, the pulse development could be achieved using retriggerable monostable multivibrators. Such multivibrators could provide the delayed timing to generate the three pulses 100 microseconds apart in response to the master frequency, i.e., in response to the control pulse. Alternatively, generation of the three pulses could be implemented using processor control, microprocessor control, or other current conventional technologies.

As shown in FIG. 1, a polarity switch SW5 is disposed between the discharge portion 140 and the output 200. The polarity switch 150 may include a double pole—double throw switch to reverse the polarity of the active patient electrodes. Alternatively, the polarity switch portion SW5 may include a voltage-controlled relay under digital control.

Those persons skilled in the art will therefore readily understand that the present invention is susceptible to a bread utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention.

Accordingly, while the present invention has been described herein in detail in relation to its exemplary embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims.

What is claimed is:

1. A stimulation apparatus for providing pulsed electrical outputs to stimulate a portion of a body of a patient, the apparatus comprising:
    a common pulse generator that generates a control pulse, the control pulse being pulsed by the common pulse generator at a master frequency;
    a pulse pair generator to generate dual trigger pulses in respective channels, the trigger pulses being generated in response to the pulse pair generator receiving the control pulse at the master frequency, each of the trigger pulses including a trio of pulses;
    a channel control that controls which channel will be active;
    a set of dual independent voltage pumps that are controlled by the channel control, each of the respective voltage pumps operating on one of the channels, each of the voltage pumps adjustably generating output pulses in response to a corresponding trigger pulse based on the control of the channel control;
    a set of active electrodes that each receive output pulses from a respective one of the voltage pumps; and
    a single ground electrode to receive at least a portion of the output pulses from at least one of the active electrodes.

2. The stimulation apparatus according to claim 1, wherein the master frequency may be adjusted from 1 pulse per second to 100 pulses per second.

3. The stimulation apparatus according to claim 1, wherein the trigger pulse includes a trio of pulses that includes 3 pulses spaced 100 microseconds apart from each other.

4. The stimulation apparatus according to claim 1, wherein the channel control further controls activation and deactivation of the channels in a sequence, the sequence based on a mode setting selected by a user.

5. The stimulation apparatus according to claim 4, wherein the mode may be an alternating mode or a continuous mode.

6. The stimulation apparatus according to claim 5, wherein the set of active electrodes includes a first active electrode and a second active electrode, and the alternating mode includes operating the first active electrode and the second active electrode alternately.

7. The stimulation apparatus according to claim 5, wherein the set of active electrodes includes a first active electrode and a second active electrode, and the continuous mode includes operating the first active electrode and the second active electrode simultaneously.

8. The stimulation apparatus according to claim 1, wherein each of the output pulses is a high voltage, low current pulse.

9. The stimulation apparatus according to claim 1, further including an intensity control portion, the intensity control portion providing control of the intensity of the output pulses generated by each voltage pump.

10. The stimulation apparatus according to claim 1, wherein the output pulses are monophasic pulses.

11. The stimulation apparatus according to claim 1, wherein the set of active electrodes and the ground electrode apply the output pulses to the patient transcutaneously.

12. The stimulation apparatus according to claim 1, further including a polarity control portion to respectively control the polarity of the output pulses from each voltage pump, the polarity control portion outputting the processed output pulses to respective active electrodes.

13. The stimulation apparatus according to claim 12, wherein the polarity control portion is a polarity switch.

14. The stimulation apparatus according to claim 1, wherein the portion of a body of a patient is at least one of nerves and muscles.

* * * * *